US008031039B2

(12) United States Patent
Sasada et al.

(10) Patent No.: US 8,031,039 B2
(45) Date of Patent: Oct. 4, 2011

(54) SEPARATE TYPE MAGNETIC SHIELD APPARATUS

(75) Inventors: Ichiro Sasada, Fukuoka (JP); Toshikazu Takeda, Tokyo (JP)

(73) Assignees: Kyushu University, National University Corporation, Fukuoka (JP); Nippon Steel Composite Co., Ltd., Tokyo (JP)

( * ) Notice: Subject to any disclaimer, the term of this patent is extended or adjusted under 35 U.S.C. 154(b) by 278 days.

(21) Appl. No.: 12/521,423

(22) PCT Filed: Dec. 27, 2007

(86) PCT No.: PCT/JP2007/075416
§ 371 (c)(1),
(2), (4) Date: Jun. 26, 2009

(87) PCT Pub. No.: WO2008/081999
PCT Pub. Date: Jul. 10, 2008

(65) Prior Publication Data
US 2010/0321138 A1   Dec. 23, 2010

(30) Foreign Application Priority Data
Dec. 28, 2006   (JP) .................................. 2006-356666

(51) Int. Cl.
*H01F 7/00* (2006.01)
*H01F 38/12* (2006.01)
*H01F 27/32* (2006.01)
*H05K 9/00* (2006.01)
(52) U.S. Cl. ..... 335/301; 174/350; 336/84 R; 336/84 M
(58) Field of Classification Search .................. 335/301, 335/304, 202, 214; 174/350, 397; 336/84 R, 336/84 M
See application file for complete search history.

(56) References Cited

U.S. PATENT DOCUMENTS
3,466,499 A * 9/1969 Beth .............................. 315/85
(Continued)

FOREIGN PATENT DOCUMENTS
JP   62-279607 A   12/1987
(Continued)

OTHER PUBLICATIONS
I. Sasada, "Magnetic Shields Employing the Magnetic Shaking Technique for Use in Weak Magnetic Field Measurements," Kyushu University, vol. 27, No. 8, pp. 855-861 (2003).
(Continued)

*Primary Examiner* — Anh Mai
*Assistant Examiner* — Mohamad Musleh
(74) *Attorney, Agent, or Firm* — Panitch Schwarze Belisario & Nadel LLP

(57) ABSTRACT

It is an object of the present invention to provide a separate type magnetic shield apparatus which has high access performance to a magnetically shielded space, in which magnetic shielding is very effectively achieved. In the separate type magnetic shield apparatus, first and second conductors 10a and 10b extending in the longitudinal axial line direction are provided on a curved magnetic shield outer side wall 3 of a first magnetic shield side wall body 2A at up and down symmetrical positions relative to the longitudinal plane Hp passing through the longitudinal axial line of the cylindrical space S to cause current to flow therethrough; first and second conductors 10c and 10d extending in the longitudinal axial line direction, on the curved magnetic shield outer side wall 3 of the second magnetic shield side wall body 2B, at up and down symmetrical positions relative to the horizontal plane Hp passing through the longitudinal axial line of the cylindrical space S to cause current to flow therethrough; and magnetic fluxes H coming horizontally to the first magnetic shield side wall body 2A and to the second magnetic shield side wall body 2B are deflected up and down by means of magnetic fields produced around the first and second conductors 10a, 10b, 10c and 10d, thereby preventing magnetic fluxes from flowing into the cylindrical space S.

21 Claims, 12 Drawing Sheets

U.S. PATENT DOCUMENTS

| | | | | | |
|---|---|---|---|---|---|
| 3,671,902 | A | * | 6/1972 | Westendorp | 336/84 R |
| 4,152,745 | A | * | 5/1979 | Eul | 361/146 |
| 4,646,046 | A | * | 2/1987 | Vavrek et al. | 335/301 |
| 4,712,067 | A | * | 12/1987 | Roschmann et al. | 324/318 |
| 4,808,957 | A | * | 2/1989 | Furukawa | 335/301 |
| 6,229,423 | B1 | * | 5/2001 | Sasada et al. | 335/301 |
| 2005/0110603 | A1 | * | 5/2005 | Tashiro et al. | 336/90 |

FOREIGN PATENT DOCUMENTS

| | | | |
|---|---|---|---|
| JP | 06167583 A | * | 6/1994 |
| JP | 2004-179550 A | | 6/2004 |
| JP | 2005283191 A | * | 10/2005 |
| JP | 2006-075372 A | | 3/2006 |

OTHER PUBLICATIONS

Y. Nakashima et al., "Magnetic Field Leakage From a 45°-Angle Magnetic Shell and a Reduction Method for a High-Performance Magnetic Shield," IEEE Transactions on Magnetics, vol. 42, No. 10, pp. 3545-3547 (2006).

T. Saito et al., "Performance of Active Compensation for a Multi-shell Shield with an Inner Passive Shell," Kyushu University, vol. 29, No. 5, pp. 567-570 (2005).

Y. Umeda et al., "Development of an Active Cancel System for Cylindrical Magnetic Shields," IEEJ Trans. FM, vol. 123, No. 8, pp. 790-796 (2003).

* cited by examiner

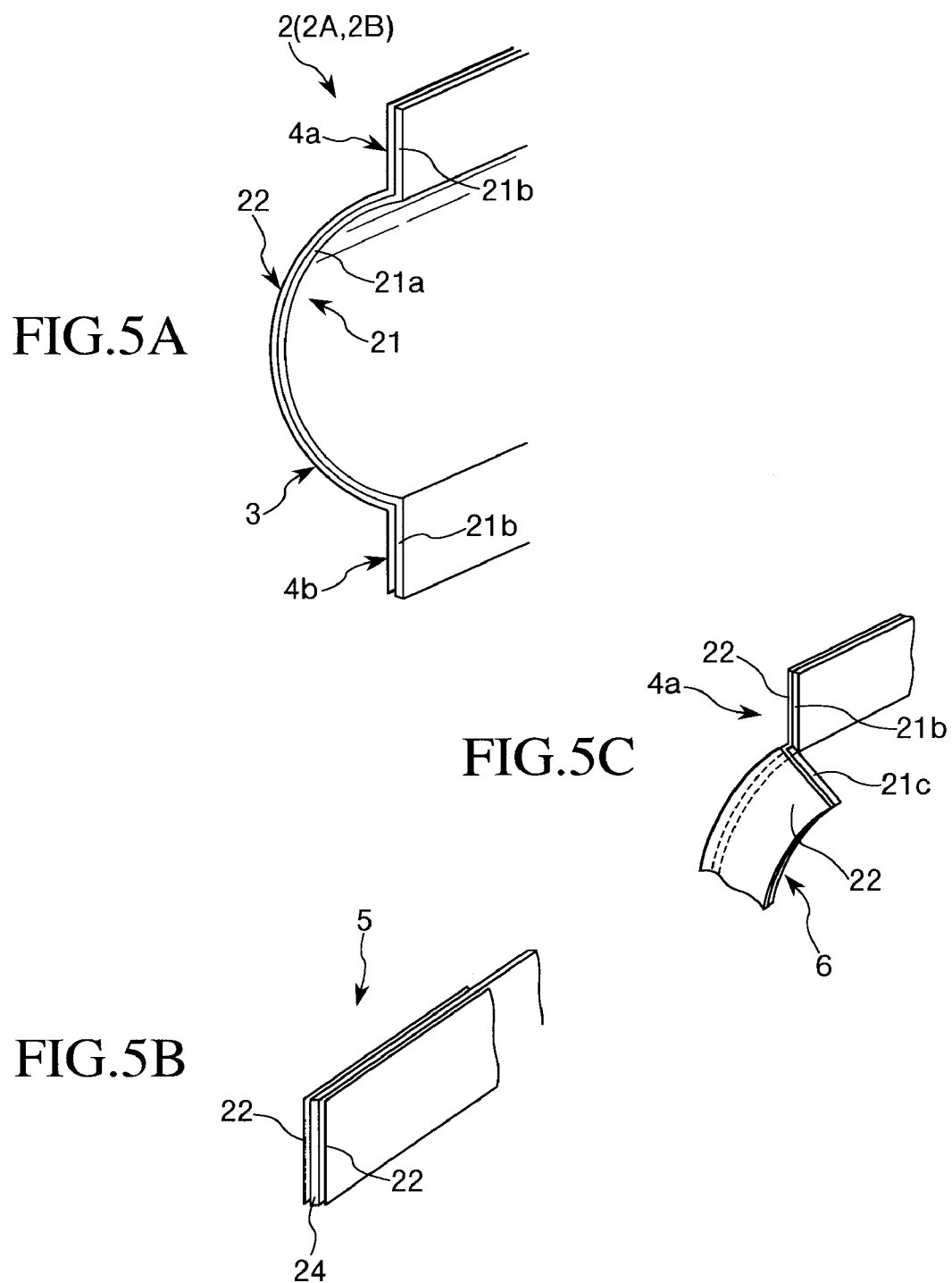

SEPARATE TYPE MAGNETIC SHIELD APPARATUS

CROSS-REFERENCE TO RELATED APPLICATION

This application is a Section 371 of International Application No. PCT/JP2007/075416, filed Dec. 27, 2007, which was published in the Japanese language on Jul. 10, 2008 under International Publication No. WO 2008/081999 A1, and the disclosure of which is incorporated herein by reference.

TECHNICAL FIELD

The present invention relates to a separate type magnetic shield apparatus applicable, for example, as an electronic beam exposure apparatus, measures taken for environmental magnetic field of an electron microscope, and in the area of measurement, human cerebral magnetic field, cardiac magnetic field measurement, furthermore, animal biological magnetism measurement, and moreover, measurement in the nano-bio-area in which magnetic beads are used as labels.

BACKGROUND ART

For example, the magnetic field emitted from a human body such as that from brain or heart contains many important real-time biological pieces of information. When the cardiac magnetic field detected by a MCG detector such as 64 channel SQUID gradiometers, the electrophysiological function of heart can be two-dimensionally mapped. It is furthermore possible to obtain overwhelmingly more accurate and more diverse diagnostic pieces of information than those available by the method based on waveform analysis of electrocardiograph, such as time and space information of current vector flowing along the irritation conduction system.

Acute myocardiac infarction which is an epitome of ischemic heart diseases is believed to be one of the three major causes of death of Japanese. Expensive high-tech medical technologies are used for the cure thereof. If more accurate and more rapid diagnosis is possible, it would bring about considerable effects not only in the remarkable reduction of medical cost but also in life-saving.

Partly because of the lapse of only a short period of time from development of the magnetocardiograph, its popularization is still in an initial stage in spite of these rich potentialities.

One of the causes of this slow progress of popularization lies in a chamber type magnetic shield room made of permalloy which is expensive and inconvenient. The magnetic screening performance is not required to be so high as that required for cerebral magnetic field measurement, but here is an increasing demand for a flexible magnetic shield apparatus which permits measurement by bringing the patient together with his or her bed.

In other words, there is a demand for development of a separate movable type high-performance magnetic shield apparatus, not of the chamber type, which is applicable without difficulty for the measurement of biological magnetism such as cardiac magnetic field issued not only from a healthy person, but also from a bedridden patient.

The present inventors have therefore developed many component technologies for the purpose of developing a cylindrical-type light and high-performance magnetic shield apparatus. A magnetic shaking technology (Non-Patent Document 1); leakage inhibition of shaking magnetic field (Non-Patent Document 2); inhibition of magnetic noise caused by an external cause entering from an opening end (Non-Patent Documents 3 and 4); and further, integral forming of magnetic shield based on lamination structure using a carbon fiber reinforced plastics (CFRP) (Patent Document 1) are included.

In general, installation of a chamber-type shield apparatus afterward in the room results in a difference in floor height so that it is not easy to carry the patient, together with his or her bed, into the apparatus.

It is therefore suggested to simply divide the cylindrical shield into two and to make it movable as described in Patent Document 2. FIG. 12 illustrates an example of the separate type shield apparatus 100 having a structure in which divided pieces are arranged one to the right and the other to the left, and are joined at upper and lower positions.

According to this example, the separate type shield apparatus 100 has a structure in which at least any of two magnetic shield divided bodies 101 (101A and 101B) formed in a right-left-symmetrical shape is made movable to permit transportation of a patient together with his or her bed into the inner space.

However, the function of magnetic shield cannot be maintained with this configuration alone. Since, in the separate type shield apparatus 100, it is necessary to install SQUID gradiometers 200, and a space is formed at the joint between the two divided bodies 101A and 101B. Therefore, magnetic fluxes passing through this space (i.e., magnetic fluxes perpendicular to the joint) cannot be passed continuously, and the magnetic shielding effect fails here.

Patent Document 1: Japanese Patent Application No. 2005-80775
Patent Document 2: Japanese Patent Application Laid-Open No. 2004-179550
Non-Patent Document 1: Ichiro SASADA, study on magnetic shaking type magnetic shield for measuring weak magnetic fields, Journal of Japan Applied Magnetism Society, 27,855-861 (2003)
Non-Patent Document 2: Nakashima Y, Kimura T, Sasada I, Magnetic field leakage from a 45° angle magnetic shell and a reduction method for a high-performance magnetic shield, IEEE Trans. on Magn. 42(10)3545-3547 (2006)
Non-Patent Document 3: Saito T, Tashiro N, Sasada I, Active compensation effect in multi-shell shield with passive shell, Journal of Japan Applied Magnetism, 29, 567-570 (2005)
Non-Patent Document 4: Umeda Y, Tashiro N, Sasada I, Application of active cancellation to cylindrical magnetic shield, Electricity Society A, 123, (8), 790-796 (2003)

DISCLOSURE OF THE INVENTION

Problems to be Solved by the Invention

It is an object of the present invention to solve the above-mentioned problems posed by the separate type shield apparatus having the configuration as shown in FIG. 12. At the same time, it is also another object of the present invention to provide a simple, compact and high-performance magnetic shield having a configuration in which disturbing magnetic fields are deflected not to enter into the space to be shielded by actively produced magnetic fluxes, and magnetic bodies are partially arranged to prevent the actively produced magnetic fields from entering the space to be shielded.

In general, a method popularly used at the time of creating a space having a low magnetic flux density in a case where magnetic fluxes are uniformly present is to flow current into conductors in the direction in which magnetic fluxes are to be ejected by arranging conductors in the space. A case where optimization is achieved by this method is illustrated in FIG. 11(a).

In this example, four conductors 10 (10a, 10b, 10c and 10d) are arranged at prescribed intervals at up-down and right-left symmetrical positions. In the drawing, current flows through the conductors 10a and 10c from the near side to the far side, and flows through the conductors 10b and 10d from the far side to the near side. For the horizontal magnetic flux H entering from left to right in FIG. 11(a), the magnetic flux line density is lower at the center portion S of the space surrounded by the four conductors 10 (10a, 10b, 10c and 10d), and it is known that magnetic shielding is accomplished there.

FIG. 11(b) illustrates, on the other hand, a configuration in which four magnetic plates A, B, C and D are arranged in a rectangular shape by providing a gap G at positions neighboring each other. In this configuration, most magnetic fluxes pass through the center portion, and the shielding effect is unavailable.

However, the configuration shown in FIG. 11(c) is achieved by combining the configuration of FIG. 11(a) and that of FIG. 11(b). As shown in FIG. 11(c), a portion where the magnetic flux line density is low at the center portion S of the space surrounded by four magnetic body plates A, B, C and D is formed in this configuration, and it is revealed that a high shielding ratio unexpected at all is available here.

The cause is that the magnetic fluxes are expelled by means of the current flowing through the conductors 10a, 10b, lac and 10d, and simultaneously, unnecessary magnetic fluxes are prevented from lapping out by the magnetic bodies A, B, C and D on the side of the space to be shielded (center portion S).

The possibility was thus revealed to localize the effect of excluding magnetic fluxes by the current to a particular direction, by properly designing the relationship between current and the magnetic bodies.

More specifically, in the configuration shown in FIG. 11(c), a combined structure of the two conductors 10a and 10c provided at upper positions and the magnetic body plates A and C expel the magnetic flux line H upward, and a combined structure of the two conductors 10b and 10d and the magnetic body plates B and D expel the magnetic flux line H downward, thus causing generation of a wide magnetic shield space S at the center.

The present invention is based on a novel finding of the present inventors as described above that proper combination of the current action and the action of magnetic bodies makes it possible to very effectively achieve a magnetic shield.

An object of the present invention is to provide a separate type magnetic shield apparatus which has a high access property to a magnetic shielding space and permit effective achievement of magnetic shielding.

Means for Solving the Problems

The above-mentioned objects of the present invention are achievable by use of the separate type magnetic shield apparatus of the present invention. In short, according to the present invention, there is provided a separate-type magnetic shield apparatus, having a plurality of magnetic shield side wall bodies in the longitudinal direction; wherein the plurality of magnetic shield side wall bodies are combined mutually to form therein a substantially cylindrical space around the longitudinal axial line extending horizontally, and at least one of the magnetic shield side wall bodies moving relative to the remaining magnetic shield side wall bodies is made separable;

wherein each of the plurality of magnetic shield side wall bodies has a magnetic shield outer side wall body having one of the magnetic bodies which are combined mutually to form therein the cylindrical space, and joint magnetic shield side walls having magnetic bodies which project from the both longitudinal end edges of the magnetic shield outer wall outwardly in the radial direction to the cylindrical space;

and wherein conductors extending in the longitudinal axial direction of the cylindrical space are provided on the magnetic shield outer wall of the magnetic shield side wall body to supply current therethrough;

and whereby disturbing magnetic fluxes entering to magnetic shield side wall bodies which would pass from one side to the other side of the magnetic shield side wall bodies are deflected upwardly or downwardly by means of the magnetic field produced around the conductors to thereby prevent the magnetic fluxes from flowing into the cylindrical space.

According to an embodiment of the present invention, a plurality of bulkhead magnetic shield members having magnetic bodies are arranged between facing joint magnetic side walls of neighboring magnetic shield side wall bodies.

According to another embodiment of the present invention, the magnetic shield outer side wall and the joint magnetic shield side wall are formed by providing magnetic bodies on a support.

According to another embodiment of the present invention, the bulkhead magnetic shield members are formed by providing magnetic bodies on a support.

According to another embodiment of the present invention, a coil is wound in the longitudinal direction thereof and in a toroidal shape around the magnetic shield side wall body, and magnetic shaking current is supplied thereto.

According to another embodiment of the present invention, a magnetic shield flange is provided at each of the both-end openings in the longitudinal direction of each magnetic shield side wall body, thereby preventing magnetic fluxes from flowing into the cylindrical space from the longitudinal end openings of the magnetic shield side wall body.

According to another embodiment of the present invention, the magnetic shield flange member is formed by providing a magnetic body on a support.

According to another embodiment of the present invention, a coil is installed on the magnetic shield flange member to cause current to flow therethrough, thereby preventing magnetic fluxes from flowing into the cylindrical space from the longitudinal openings of the magnetic shield side wall body.

According to another embodiment of the present invention, a coil is wound around the joint magnetic shield side wall oppositely arranged of the neighboring magnetic shield bodies in the axial direction, and current is supplied therethrough, thereby preventing magnetic fluxes from flowing from the gap formed between the joint magnetic shield side walls arranged oppositely of the neighboring magnetic shield side wall bodies.

According to another embodiment of the present invention, the cylindrical space is formed by being surrounded by two, four, six or eight magnetic shield wall bodies.

According to another embodiment of the present invention, the magnetic shield side wall bodies surrounding the cylindrical space have an identical size and shape.

According to a preferred embodiment of the present invention, there is provided a separate type magnetic shield apparatus comprising a first magnetic shield side wall body and a second magnetic shield side wall body; wherein the first magnetic shield side wall body and the second magnetic shield side wall body form a substantially cylindrical space around the longitudinal axial line extending horizontally in the interior in an oppositely arranged state; and at least any of the magnetic shield side wall bodies moves and is separable from the other magnetic shield side wall body;

wherein the first and second magnetic shield side wall bodies each has a curved magnetic shield outer side wall which has a magnetic body forming the cylindrical space in the interior in the oppositely arranged state, and joint magnetic shield side walls having magnetic bodies which project vertically from the upper and lower end edges of the curved magnetic shield outer side wall and are spaced apart from each other and facing each other in a oppositely arranged state;

wherein first and second conductors extending in the longitudinal axial line direction are provided on the curved magnetic shield outer side wall of the first magnetic shield side wall body to cause current to flow;

wherein first and second conductors extending in the longitudinal axial line are provided on the curved magnetic shield outer side wall of the second magnetic shield side wall body to cause current to flow;

and whereby disturbing magnetic fluxes coming from the first magnetic shield side wall body horizontally to the second magnetic shield side wall body are deflected up and down by means of magnetic fluxes produced around the first and second conductors, thereby preventing the magnetic fluxes from flowing into the cylindrical space.

Preferably, according to an embodiment, the first magnetic shield side wall body and the second magnetic shield side wall body have right-left symmetric shapes relative to a vertical plane passing through the longitudinal axial line of the cylindrical space.

According to another embodiment, a plurality of bulkhead magnetic shield members each having a magnetic body arranged between the joint magnetic shield side walls opposing to each other of the first and second magnetic shield side wall bodies.

According to another embodiment, the curved magnetic shield outer side wall and the joint magnetic shield side wall are formed by providing a magnetic body in each of the supports.

According to another embodiment, the bulkhead magnetic shield member is formed by providing a magnetic body in each support.

According to another embodiment, a coil is wound in a toroidal shape in the axial line direction around the first and second shield side wall bodies.

According to another embodiment, magnetic shield flange members are provided in the axial direction end openings of the first and second shield side wall bodies, thereby preventing magnetic fluxes from flowing from the axial-direction end openings of the first and second shield side wall bodies into the cylindrical space.

According to another embodiment, the magnetic shield flange member is formed by providing a magnetic body in each of the supports.

According to another embodiment, a coil is installed on the magnetic shield flange member to cause current to flow therethrough, thereby preventing magnetic fluxes from the axial-direction and openings of the first and second magnetic shield side wall bodies into the cylindrical space.

According to another embodiment, around the joint magnetic shield side wall oppositely arranged of the first and second magnetic shield side wall bodies, a coil is wound in the axial line direction to cause current to flow therethrough, thereby preventing magnetic fluxes from flowing from the gap formed between the joint magnetic shield side walls oppositely arranged of the first and second magnetic shield side wall bodies into the cylindrical space.

Functional Effects of the Invention

The separate type magnetic shield apparatus of the present invention has a high access performance to a magnetic shield space and permits very effective achievement of magnetic shield.

BRIEF DESCRIPTION OF THE DRAWINGS

FIG. 1(*b*) is a schematic configuration view of the separate type magnetic shield apparatus.

FIG. 5(*a*) is a view for describing the configuration of the magnetic shield side wall body; FIG. 5(*b*) is a view for describing the configuration of a bulkhead magnetic shield member; and FIG. 5(*c*) is a view for describing the configuration of a magnetic shield flange member.

FIG. 7(*b*) is a view for describing the method for determining current to be supplied to a conductor.

BEST MODE FOR CARRYING OUT THE INVENTION

The separate type magnetic shield apparatus of the present invention will now be described further in detail with reference to the drawings.

Embodiment 1

(Overall Configuration of the Separate Type Magnetic Shield Apparatus)

Figure 1A:
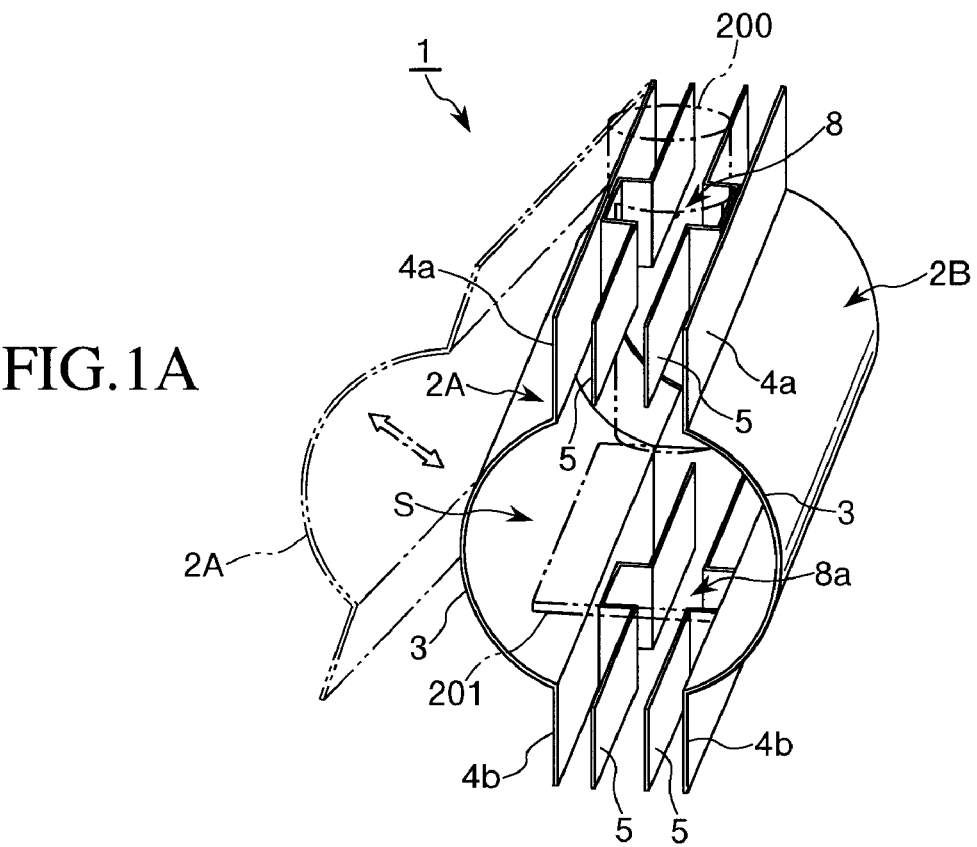
FIG. 1(*a*) is an overall configuration view of an embodiment of the separate type magnetic shield apparatus of the present invention.

FIG. 1(*a*) is an overall configuration view illustrating an embodiment of the separate type magnetic shield apparatus 1 of the present invention. FIG. 1(*b*) is a schematic configuration view illustrating only main parts for describing the overall configuration of the separate type magnetic shield apparatus 1 shown in FIG. 1(a).

In the separate type magnetic shield apparatus 1 of the present invention, the layout is such that the longitudinal direction of the overall structure is horizontal, and the apparatus has a plurality of magnetic shield side wall bodies 2 extending in the longitudinal direction. According to the embodiment shown in FIGS. 1(a) and (b), the magnetic shield side wall body 2 has a first magnetic shield side wall body 2A and a second magnetic shield side wall body 2B extending in the longitudinal direction.

According to this embodiment, the first magnetic shield side wall body 2A and the second magnetic shield side wall body 2B form, in a state arranged oppositely as shown in the drawing, a substantially cylindrical space S around a longitudinal axial line Y-Y extending horizontally in the interior.

Although the arrangement of the first magnetic shield side wall body 2A and the second magnetic shield side wall body 2B is not limited to the following one, these bodies 2A and 2B should preferably be arranged right-left symmetrically relative to a vertical plane Vp passing through the longitudinal axial line Y-Y of the cylindrical space S. Also preferably, the first magnetic shield side wall body 2A and the second magnetic shield side wall body 2B are arranged up-down symmetrically relative to a horizontal plane Hp passing through the longitudinal axial line of the cylindrical space S.

When the first magnetic shield side wall body 2A and the second magnetic shield side wall body 2B are arranged right-left and up-down symmetrically as in this embodiment, a portion having the lowest density of magnetic flux lines is formed substantially at the center of the cylindrical space S of the separate type magnetic shield apparatus 1 as described later in more detail. In this case, it is possible to-provide a space having a magnetic gradient of substantially null.

Figure 12:
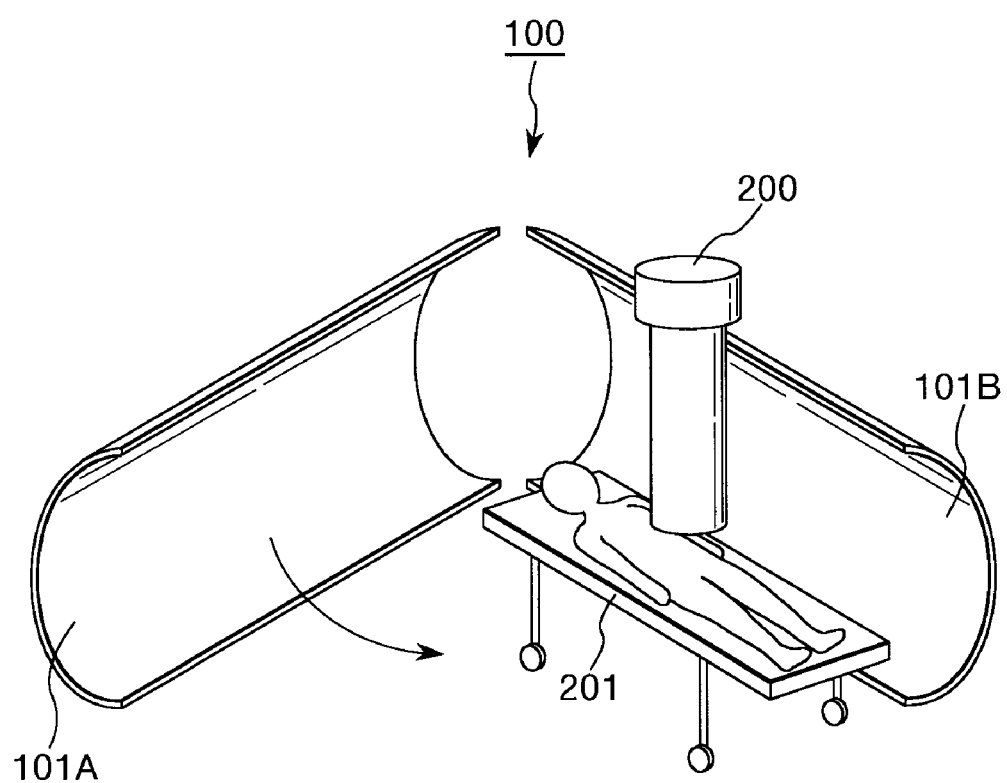
FIG. 12 is an overall configuration view illustrating an example of the conventional separate type magnetic shield apparatus.

In this embodiment, for the separate type magnetic shield apparatus 1, as in the case of the separate type magnetic shield apparatus 100 described with reference to FIG. 12, any of the first magnetic shield side wall body 2A and the second magnetic shield side wall body 2B, or both the magnetic shield side wall bodies 2A and 2B can be made movable. In this embodiment, the first magnetic shield side wall body 2A is made movable, and the second magnetic shield side wall body 2B is fixed. The configuration is not however limited to this, but the reverse is applicable.

Figure 1B:
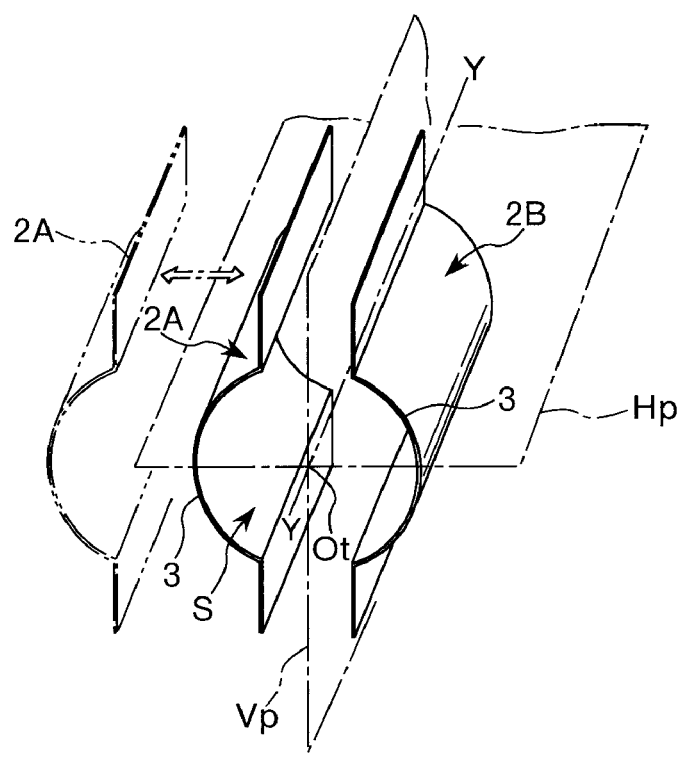

As to the manner of separation, for example, as shown by a one-point chain line in FIG. 1(a), the movable magnetic shield side wall body 2A may rotate around an end in the longitudinal direction, or as shown by a one-point chain line in FIG. 1(b), the configuration may be such that the movable body 2A moves in parallel to the horizontal direction relative to the other magnetic shield side wall body 2b.

Figure 2:
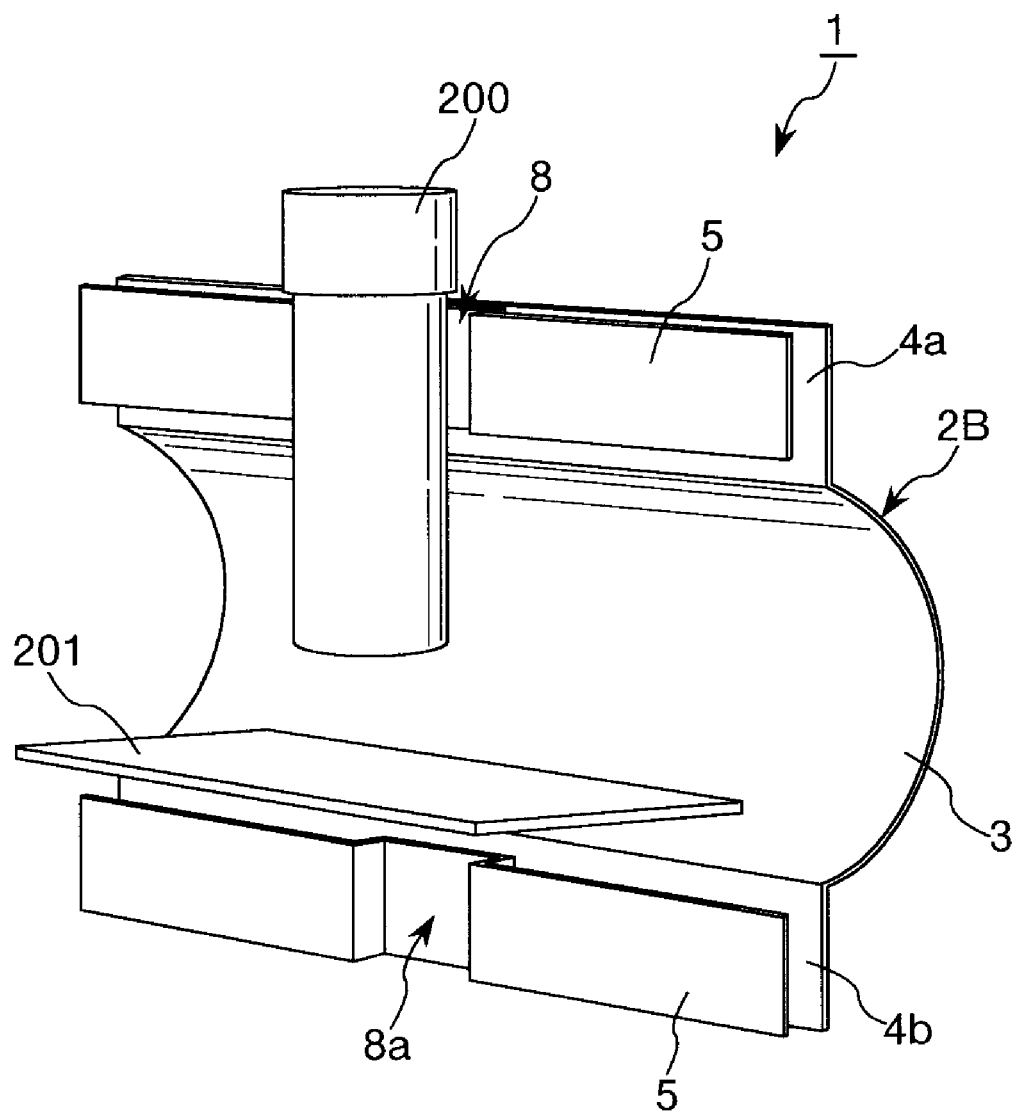
FIG. 2 illustrates a state of the separate type magnetic shield apparatus shown in FIG. 1 in which one of the magnetic shield side wall bodies is removed.

FIG. 2 illustrates a state in which the first magnetic shield side wall body 2A is removed, to show the interior of the separate type magnetic shield apparatus 1.

In this embodiment, as shown in FIGS. 1 and 2, a MCG detector 200 having a substantially cylindrical shape such as SQUID gradiometers is installed from above of the apparatus, at a position substantially central in the longitudinal direction of the separate type magnetic shield apparatus by inserting the MCG detector 200 into the internal space S of the separate type magnetic shield apparatus 1. A bed 201 for placing a subject patient is provided spaced apart from the lower end of the magnetocardiograph 200 by a prescribed distance. The bed 201 may be fixed to the fixed second magnetic shield side wall body 2B. It is possible to use a configuration, as the case may be, in which a fixed bed is not installed on the separate type magnetic shield apparatus 1 itself, but a bed holding the subject patient on it is carried into the separate type magnetic shield apparatus 1. According to the separate type magnetic shield apparatus 1 of the present embodiment, the subject patient or the subject patient and the bed can be brought into the separate type magnetic shield apparatus 1 in a state in which the first magnetic shield side wall body 2A and the second magnetic shield side wall body 2B are separated, thus providing very convenient operation.

(Magnetic Shield Side Wall Body)

The magnetic shield side wall bodies 2 (2A and 2B) will now be described.

As described above, the first magnetic shield side wall body 2A and the second magnetic shield side wall body 2B in this embodiment should preferably have a right-left and up-down symmetrical shape. In the following description, therefore, when it is not required to distinguish between the first and the second magnetic shield side wall bodies 2A and 2B, the first and the second magnetic shield side wall bodies 2A and 2B will be described generally as "the magnetic shield side wall bodies 2".

Referring to FIGS. 1 and 2, the magnetic shield side wall bodies 2 have a magnetic shield outer side wall 3, having a curved shape in this embodiment, for forming a cylindrical space S of the separate type magnetic shield apparatus 1, and flat joint magnetic shield side walls 4 (4a and 4b) vertically projecting upwardly and downwardly from the upper and the lower edges of these curved magnetic shield outer side wall 3. Since, as described above, the first and the second magnetic shield side wall bodies 2A and 2B have a shape right-left and up-down symmetrical, the joint magnetic shield side walls 4a and 4b have also the same shape and dimensions.

In this specification for convenience sake, the inner peripheral surface side forming a concave surface of the curved magnetic shield outer side wall 3 is called the inner side, and the outer peripheral surface side forming a convex surface is called the outer side.

When the first magnetic shield side wall body 2A and the second magnetic shield side wall body 2B are arranged in an opposite shape in the aforementioned configuration, the both curved magnetic shield outer side walls 3 and 3 are oppositely arranged, and in the interior, form a substantially cylindrical space S around the longitudinal axial lines Y-Y extending horizontally. In this case, the both joint magnetic shield side walls 4 (4a and 4a) provided above the curved magnetic shield outer side wall are arranged apart from each other by a prescribed distance (w) (see FIG. 4).

The MCG detector 200 is therefore installed by inserting it from the gap of the both joint magnetic shield side walls 4a and 4a formed at about the center in the longitudinal direction of the separate type magnetic shield apparatus 1 into the interior of the separate type magnetic shield apparatus 1.

The gap between the both joint magnetic shield side walls 4a and 4a positioned above should preferably be the narrowest possible gap as described later in detail. For this purpose, as is understood by referring to FIGS. 1 and 4, a plurality of, or two in this embodiment, bulkhead magnetic shield members 5 are arranged at equal intervals (w1), extending in the longitudinal direction of the separate type magnetic shield apparatus 1 and at substantially the same height position as the joint magnetic shield side walls 4a and 4a in the gap between the both joint magnetic shield side walls 4a and 4a. By providing these bulkhead magnetic shield members, there is available a function of preventing a disturbing magnetic field coming from the Y-Y axial direction (see FIG. 1(b)) from flowing into the cylindrical space.

Figure 4:
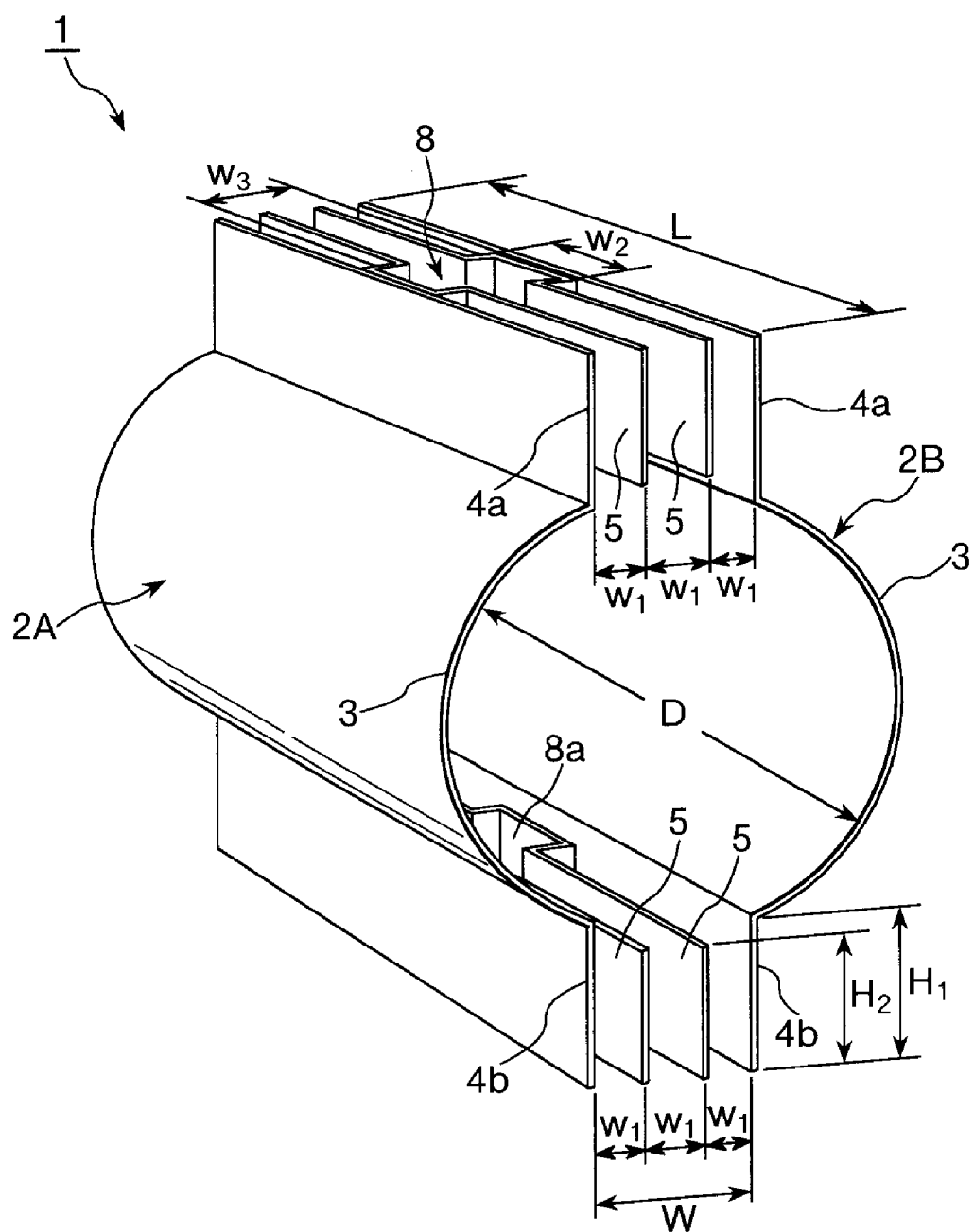
FIG. 4 is a schematic configuration view for describing the concrete configuration of the separate type magnetic shield apparatus of the present invention.

As is well understood by referring to FIGS. 1 and 4, for the purpose of attaching the MCG detector 200 to the separate type magnetic shield apparatus 1, at the position of installation of the MCG detector, the bulkhead magnetic shield member 5 is manufactured by curving it in the joint magnetic shield side wall 4a side into a ⊐-shape, and forms an attaching opening 8 for the MCG detector 200.

In this embodiment also, as described above, a shape symmetrical in the right-left direction and the up-down direction is achieved so as to form a portion with the lowest density of magnetic flux lines at almost the center of the cylindrical space S of the separate type magnetic shield apparatus 1 and so as to achieve a magnetic gradient of substantially null.

In this embodiment, therefore, as shown in FIGS. 1 and 2, a plurality of (two in this embodiment) bulkhead magnetic shield members 5 extending in the longitudinal direction of the separate type magnetic shield apparatus 1 are arranged at equal intervals (w1) even in the gap between the both joint magnetic shield side walls 4b and 4b arranged below where a MCG detector 200 is never installed. As in the structure of the gap between the two joint magnetic shield side walls 4a and 4a above, the bulkhead magnetic shield members 5 form a ⊐-shaped curve to prepare an opening 8a.

Varied Embodiment

Figure 3:
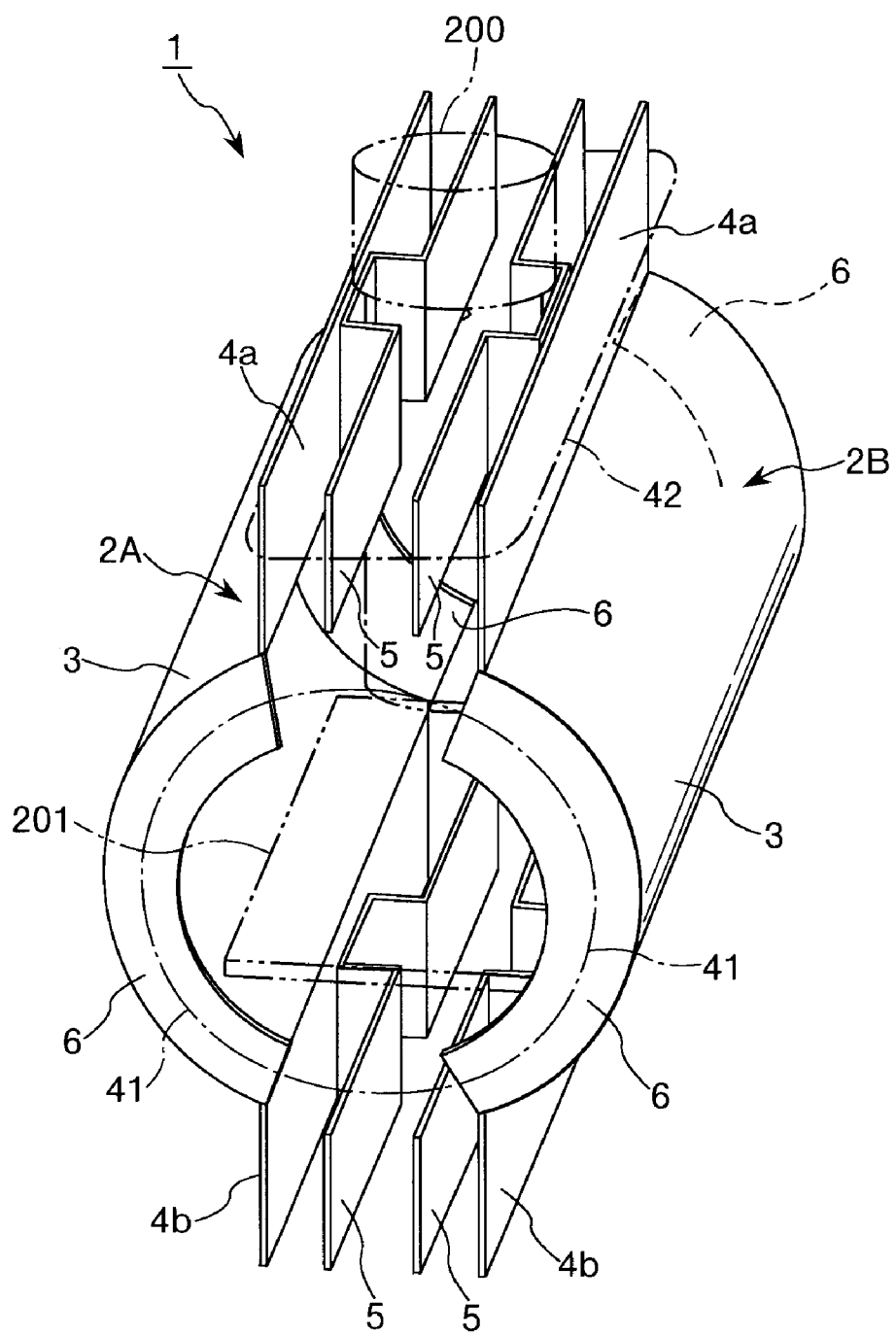
FIG. 3 is an overall configuration view of another embodiment of the separate type magnetic shield apparatus of the present invention.

As a varied one of this embodiment, as shown in FIG. 3, magnetic shield flange members 6 may be provided at both end openings in the axial line direction of the first and the second magnetic shield side wall bodies 2. More specifically, flange members 6 having a prescribed width are provided at both ends in the longitudinal direction of the curved magnetic shield outer side wall 3 in projection into the cylindrical space S and in the radial direction.

This flange member 6 has a function of reinforcing the magnetic shield side wall bodies 2. Particularly, installation of the flange member 6 gives a function of preventing a disturbing magnetic field coming from the Y-Y axial direction (see FIG. 1(b)) from flowing into the cylindrical space S. As described later, it is now possible to supply current by winding a coil 41 around this flange member 6, and further, to inhibit the disturbing magnetic field coming from the Y-Y axial direction.

(Concrete Structure of Magnetic Shield Side Wall Body)

A concrete structure of the magnetic shield side wall body 2 will now be described.

As shown in FIG. 5(a), the magnetic shield side wall bodies 2 (2A and 2B) composed of the curved magnetic outer side wall 3 and the upper and the lower joint magnetic shield side walls 4a and 4b can be composed of supports 21 having the same shape as the curved magnetic shield outer side walls 3 and the upper and the lower joint magnetic shield side walls 4 (4a and 4b), and magnetic bodies 22 arranged on these supports 21 (outer surface and/or inner surface). In FIG. 5(a), layered magnetic bodies 22 are arranged only on the outer surface, forming magnetic body layers. In other words, the supports 21 have a curved member 21a and joint members 21b vertically projecting from the curved member 21a up and down, and magnetic body layers 22 are arranged on the outer peripheral surface of the curved member 21a and on the outer surface of the joint member 21b.

The bulkhead magnetic shield member 5 is also formed, as shown in FIG. 5(b), by arranging magnetic bodies 22 on the surface (inner surface and/or outer surface) of the support 24 having the same shape as the member 5. In this embodiment, the magnetic bodies 22 are provided on the both surfaces.

The magnetic shield flange member 6 can also be composed of, as shown in FIG. 5(c), a support 21c having the same shape as the member 6, and magnetic bodies 22 arranged on the surface (outer surface and/or inner surface) of this support 21c. According to FIG. 5(c), the magnetic bodies 22 are arranged only on the outer surface, thus forming the magnetic body layer. The support 21c is made integral with the curved member support 21a of the aforementioned curved magnetic shield outer side wall 3.

As the supports 21 and 24, preferably, paper, resins, FRP, nonmagnetic metals, and various other materials are applicable. In this embodiment, the supports 21 and 24 are prepared from carbon fiber reinforced plastics.

For the magnetic body 22, a magnetic material such as permalloy is applicable. For weight reduction, however, a Co-based amorphous magnetic thin strip such as Metglas 2705M (name of commercial product: Metglas, Inc.) is suitably applicable as the magnetic body 22.

The magnetic body layer composing the magnetic body 22 should preferably be composed by laminating a magnetic thin strips as described above into layers. As the magnetic body layer 22, as described later in detail, as in the configuration described later, a plurality of magnetic body layers which should preferably be thicker than 20 μm and thinner than 500 μm are laminated into layers.

Varied Embodiment

Figure 6A:
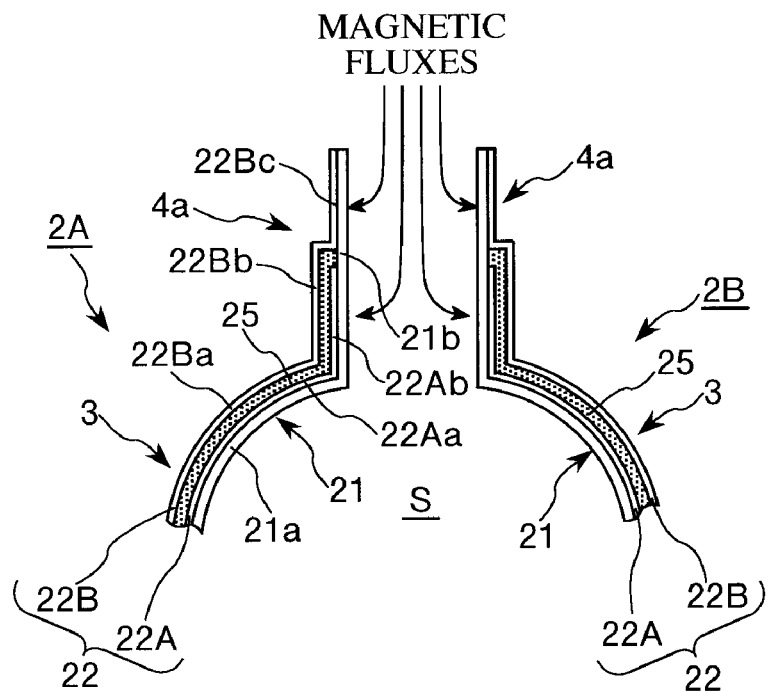
FIGS. 6(*a*) and (*b*) are views for describing the configurations of other embodiments of a magnetic shield side wall body.

By achieving a lamination structure as shown in FIG. 6(a), it is possible to efficiently prevent a disturbing magnetic field coming from above from flowing into the cylindrical space S via the gap between the both joint magnetic shield side walls 4a and 4a.

FIG. 6(a) illustrates only the upper portions of the first and the second magnetic shield side wall bodies 2A and 2B, omitting the lower portions. However, a similar structure may be used for the lower portions. In this case, disturbing magnetic fields coming from below can be efficiently prevented from flowing into the cylindrical space S via the gap between the both joint magnetic shield side walls 4b and 4b.

Only the lamination structure of the upper portions of the first and the second magnetic shield side wall bodies 2A and 2B will be described with reference to FIG. 6(a). According to this embodiment, magnetic bodies 22 are arranged in layers on the surface of the supports 21 having the same shape as the curved magnetic shield outer side layers 3 and the upper and the lower joint magnetic shield side walls 4 (4a and 4a), on the outer surface of the supports 21 in this embodiment, thus forming magnetic body layers.

According to this embodiment, the magnetic body 22 is composed of an inner magnetic body layer 22A and an outer magnetic body layer 22B bonded with a bond such as epoxy resin adhesive 25 on the outside of this inner magnetic body layer 22A. The inner magnetic body layer 22A and the outer magnetic body layer 22B themselves can be composed by piling up 10 to 30 magnetic thin strips each having a thickness of 20 μm, or depending upon the size of the prepared side wall body to be prepared, by laminating further more layers, or furthermore piling up two or more such laminations.

Description will be made further in detail. In this embodiment, the inner magnetic body layer 22A is formed of a magnetic body layer 22Aa fixedly arranged on the curved member 21a of the support 21, and a magnetic body layer 22Ab fixedly arranged on the joint member 21b, while extending to halfway upward from the magnetic body layer 22Aa to the joint member 21b of the support.

The outer magnetic body layer 22B is formed, on the other hand, of a magnetic body layer 22Ba fixedly arranged on the magnetic body layer 22Aa of the inner magnetic body layer 22A by an adhesive 25, a magnetic body layer 22Bb fixedly arranged on the magnetic body layer 22Ab of the inner magnetic body layer 22A by the adhesive 25 while extending upward from the magnetic body layer 22Ba, and a magnetic body layer 22Bc fixedly arranged on a portion of the joint member 21b further above where the magnetic body layer 22Ab of the inner magnetic body layer 22A is not fixedly arranged.

The disturbing magnetic fields flowing through the gap between the both joint magnetic shield side walls 4a and 4a into the cylindrical space S are therefore first attracted by the magnetic body layer 22Bc of the outer magnetic body layer 22B formed on the joint magnetic shield side wall 4a, and flow to the magnetic body layer Ba via the magnetic body layer 22Bb, i.e., through the outer magnetic body layer 22B, whereby the flow into the cylindrical space S is prevented. Furthermore, the disturbing magnetic fields flowing into the cylindrical space S are attracted by the magnetic body layer 22Ab of the inner magnetic body layer 22A formed on the joint magnetic shield side wall 4a, and the flow to the magnetic body layer 22Aa, i.e., to the inner magnetic body layer 22A, whereby the flow into the cylindrical space S is prevented.

As described above, the same structure may be used for the lower portions of the first and the second magnetic shield side wall bodies 2A and 2B. In this case, the disturbing magnetic fields coming from below can be efficiently prevented from flowing through the gap between the both joint magnetic shield side walls 4b and 4b into the cylindrical space S.

Varied Embodiment

According to further another embodiment, furthermore preferably as described in Patent Document 1 described in this specification in the section of conventional art, magnetic shaking current can be caused to flow at least through the curved magnetic shield outer side wall 3 of the magnetic shield side wall body 2.

In this case, a magnetic material having square magnetization property is applicable as a magnetic body 22. As such a magnetic body, the aforementioned Co-based amorphous magnetic thin strip such as Metglas 2705M is suitably applicable.

Figure 6B:
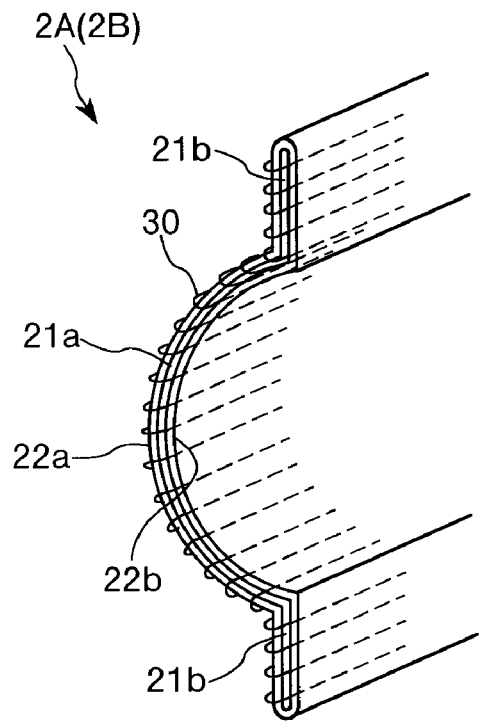

In this embodiment, particularly as shown in FIG. 6(b), a magnetic thin strip such as Metglas 2705M having a width of 50.8 mm and a thickness of 0.02 mm is arranged by continuously winding, to cover the inner peripheral surface and the outer peripheral surface of the curved member 21a in the support 21, and further, to cover the entire inner and outer surfaces of the joint member 21b. This forms a laminated magnetic body 22, i.e., a magnetic body layers 22a and 22b surrounding the support 21. The magnetic body layer 22 should have a thickness of at least 1 μm. Usually, however, it has a thickness smaller than 2 mm. The magnetic body layer 22 should preferably have a lamination structure prepared by laminating a plurality of magnetic body layers each having a thickness thicker than 20 μm and thinner than 500 μm.

Furthermore, as shown in FIG. 6(b), a coil 30 for magnetic shaking is wound. The coil 30 is wound around at least a part of the magnetic body layer 22 in a toroidal shape.

More specifically, it suffices to wind the coil so as to surround the outer magnetic body layer, i.e., to surround the outer layer of the magnetic body layers and the support 21 in the axial line direction. The manner of winding the coil is not limited to the above, but the coil wire may be wound so as to surround the inner layer 22b of the magnetic body layer 22 and the support 21 in the axial line direction.

A shaking current is supplied to the shaking magnetic field generating coil 30 of each magnetic shield side wall body 2 so as to give to the magnetic body layer 22 a shaking time of, for example, at least 50 Hz of commercial frequency and up to 10 kHz.

(Concrete Dimensions of Separate Type Magnetic Shield Apparatus)

The separate type magnetic shield apparatus prepared in this embodiment had the following concrete dimensions.

The magnetic shield side wall body 2 used a carbon fiber reinforced plastic composite material having a thickness of 5 mm as a support 21, and composed of a Metglas having a width of 50.8 mm and a thickness of 0.02 mm wound on the inner and the outer peripheral surfaces of the curved member 21a of the support 21, and further on the inner and the outer surfaces of the joint member 21b so as to cover the entire surface of the support 21.

Concrete Example:

The prepared magnetic shield side wall body 2 had the following concrete dimensions: While referring to FIG. 4:

| | |
|---|---|
| Inside diameter (D) of the curved magnetic shield outer side wall 3: | 60 cm |
| Axial length (L) of the curved magnetic shield outer side wall 3: | 180 cm |
| Width (H1) of the joint magnetic shield side wall 4: | 20 cm |
| Interval (W) between the joint magnetic shield side walls 4 and 4: | 30 cm |
| Width (H2) of the bulkhead magnetic shield member 5: | 20 cm |
| Interval (w1) of installation between the bulkhead magnetic shield members 5: | 10 cm |
| Width (w2) of the opening 8 of the bulkhead magnetic shield member 5: | 28 cm |
| Width (w3) of the opening 8 of the bulkhead magnetic shield member 5: | 28 cm |

(Magnetic Shield)

Figure 11A:
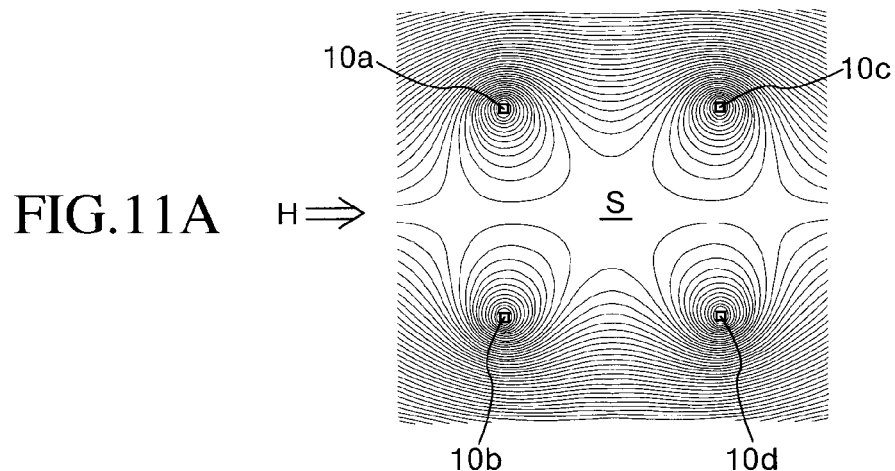
FIGS. 11(*a*) to (*c*) are magnetic flux diagrams for describing the principle of the present invention.
Figure 11B:
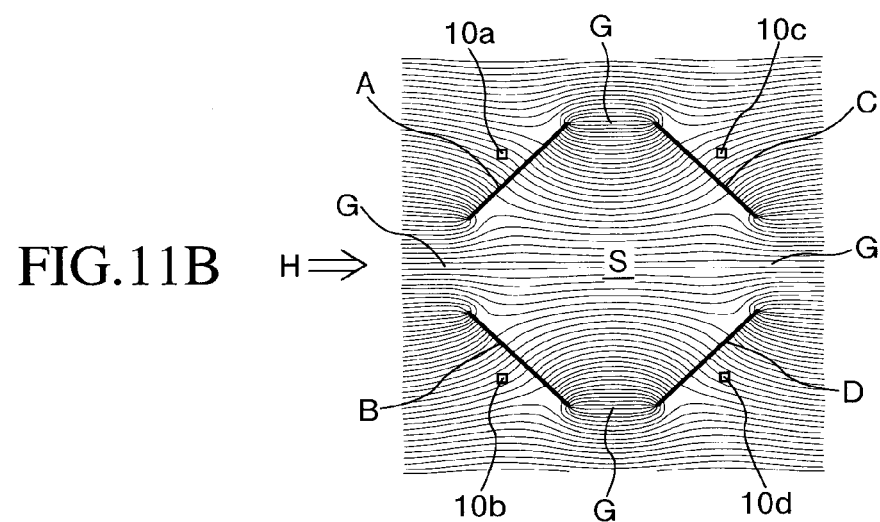
Figure 11C:
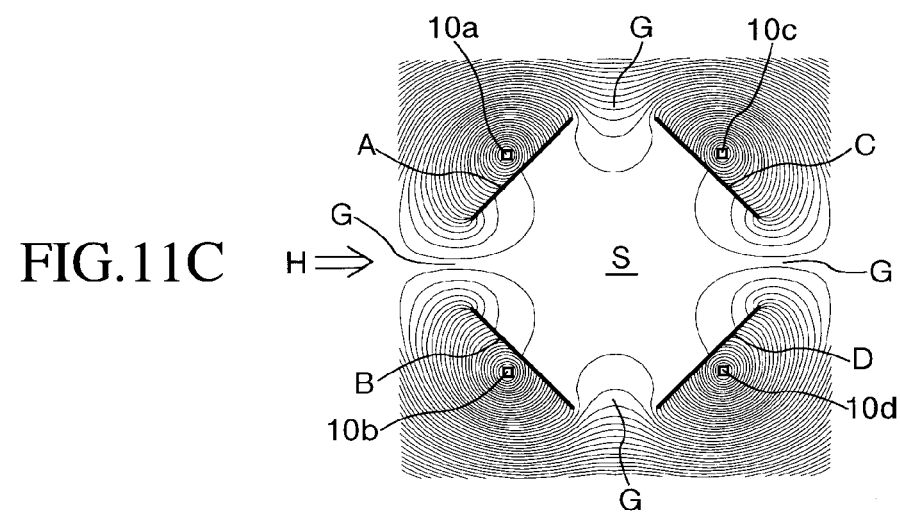

The magnetic shield of the separate type magnetic shield apparatus 1 forming a feature of the present invention will now be described. The present invention is based on the-utilization of the principle of shielding effect described above with reference to FIG. 11(c).

Figure 7A:
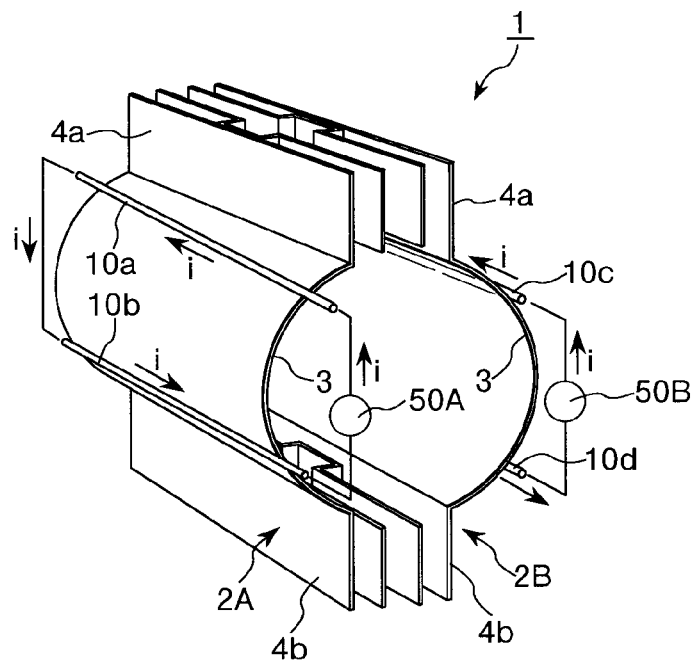
FIG. 7(*a*) is an overall configuration view of an embodiment for describing the configuration of a characteristic portion of the separate type magnetic shield apparatus of the present invention.

According to the present invention, as shown in FIG. 7(a), conductors 10 (10a, 10b, 10c and 10d) are arranged on the outer peripheral surfaces of the curved magnetic shield outer side walls 3 and 3 of the first and the second magnetic shield side wall bodies 2A and 2B in the separate type magnetic shield apparatus 1 having the above-mentioned configuration. Also according to this embodiment, the conductors 10a and 10b and the conductors 10c and 10d are connected into coil shapes, and a prescribed current i is supplied thereto by power sources 50 (50A and 50B).

In this embodiment, the current i of the same intensity is supplied by the power sources 50 (50A and 50B) to the conductors 10a and 10b and the conductors 10c and 10d, and this can be varied in response to the necessity, and the resultant current can be adjusted to an optimum value.

In this embodiment, the four conductors 10a, 10b, 10c and 10d are arranged at prescribed intervals up and down, and right and left. A current is supplied to the conductors 10a and 10c from the near side to the far side in the drawing, and to the conductors 10b and 20d from the far side to the near side.

Also in this embodiment, the conductors a and b, and the conductors c and d are respectively composed of 20-turn coils, and a current of 10 to 20 A is supplied in total to each coil, giving a satisfactory result.

Figure 8:
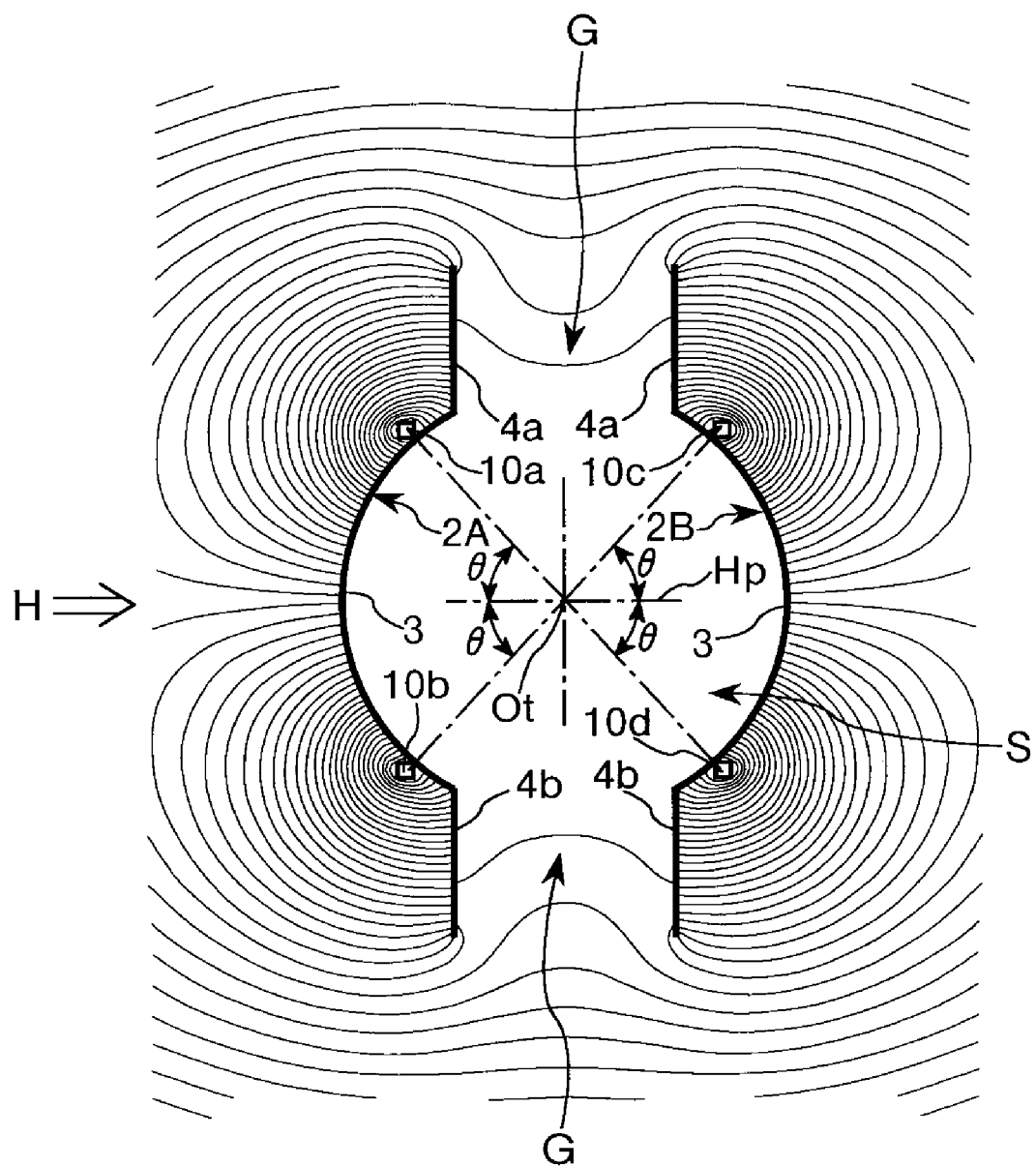
FIG. 8 is a magnetic flux line diagram in a case according to the configuration of the present invention.

According to this embodiment, in other words, referring to FIG. 8, the first and the second conductors 10a and 10b extending in the longitudinal axial line direction are provided at positions vertically symmetrical relative to a horizontal plane Hp passing through a longitudinal axial line Y-Y of the cylindrical space S on the curved magnetic shield outer side wall 3 of the first magnetic shield side wall body 2A. Similarly, the first and the second conductors 10c and 10d extending in the longitudinal axial line direction are provided at positions vertically symmetrical relative to a horizontal plane Hp passing through the longitudinal axial line Y-Y of the cylindrical space S on the curved magnetic shield outer side wall 3 of the second magnetic shield side wall body 2B.

A current is caused to flow to the conductors 10a and 10c in the same direction, and to the conductors 10b and 10d in the same direction. In this case, the current flowing to the conductors 10a and 10c and the current flowing to the conductors 10b and 10d are different in direction.

This causes vertical deflection of a magnetic flux (H) formed horizontally from the first magnetic shield side wall body 2A to the second magnetic shield side wall body 2B to up and down directions by means of magnetic fields produced around the first and the second conductors 10a and 10b, and the conductors 10c and 10d, thereby preventing the flow of the magnetic fluxes into the cylindrical space S.

(Determining Method of Current)

Figure 7B:
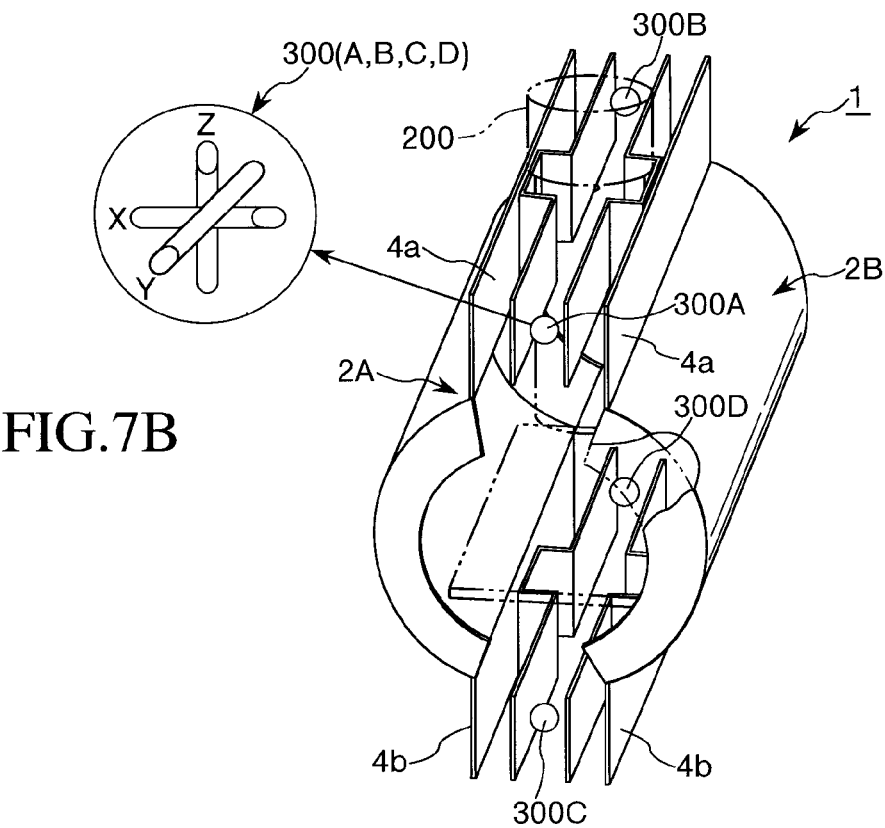

An example of the determining method of current will now be described with reference to FIG. 7(b).

In this embodiment, the X-axis is in a direction perpendicular to the shield side wall extending horizontally; the Y-axis is in the cylindrical axis direction (i.e., the longitudinal axes Y-Y direction of the cylindrical space S in FIG. 1(b)); and the Z-axis is in the vertical direction.

The magnetic sensor 300 may be flux gate magnetic field sensors or the like. In this embodiment, a tri-axial magnetic field sensor which is a magnetic field sensor based on the combination of the perpendicular axes X, Y and Z is used.

In this embodiment, furthermore, four magnetic field sensors 300 (300A, 300B, 300C and 300D) are installed in an upper gap formed by the joint magnetic shield side walls 4a and 4a of the separate type magnetic shield apparatus 1, or more specifically in this embodiment, at two positions near the longitudinal both ends and at two positions similarly in the lower gap formed by the joint magnetic shield side walls 4b and 4b. The magnetic field sensors 300 may be installed at two positions in the upper and lower portions as the case may be.

Sums of the individual components measured by the individual magnetic field sensors are calculated and averaged. For example, current for the side conductors (coils) 10a, 10b, 10c and 10d can be determined from average values of X-axis-direction values x1, x2, x3 and x4 of the individual magnetic field sensors 300. The technology of controlling the current for each conductor by using, for example, a PID control system is publicly known, and a further description is omitted here.

(Magnetic Shielding Effect)

FIG. 8 is a magnetic flux line diagram illustrating the magnetic shielding effect based on the present invention when a current is supplied to the conductors 10a, 10b, 10c and 10d.

Optimum positions of the conductors 10a, 10b, 10c and 10d are appropriately determined through experiments or the like with due regard to the configuration of the separate type magnetic shield apparatus 1. Usually, as shown in FIG. 8, a position at 30° to 60°, ordinarily at 45° relative to the horizontal plane Hp is preferable. The position is not however limited to this range.

As understood from FIG. 8, adoption of the above-mentioned configuration causes magnetic fluxes (H) entering from left to right in FIG. 8 to be deflected vertically under the effect of the magnetic field produced by the conductors 10a, 10b, 10c and 10d and the fluxes never pass through the curved magnetic shield outer side wall 3. The configuration of the present invention permits achievement of the shielding effect.

Figure 9:
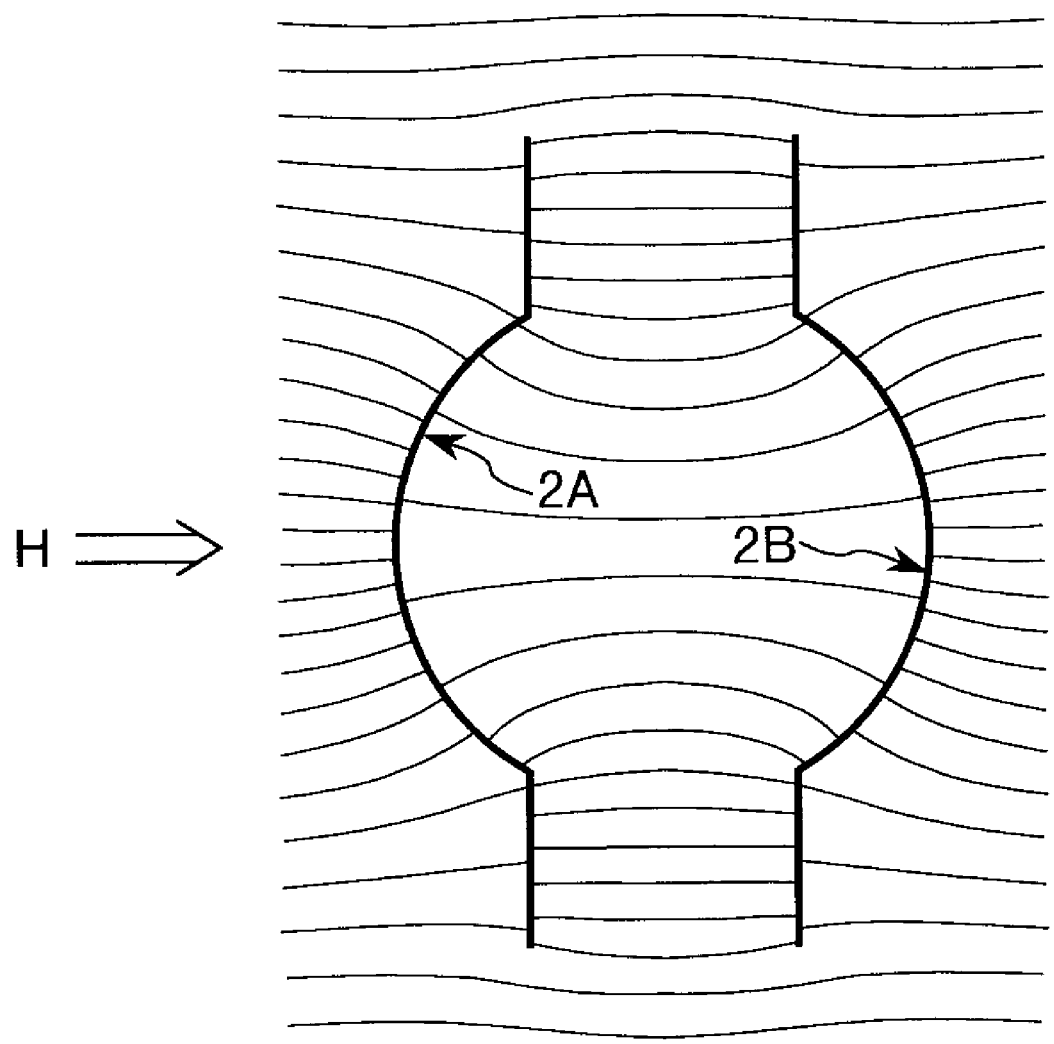
FIG. 9 is a magnetic flux line diagram in a case where the configuration of the present invention is not adopted.

As described above, on the other hand, in a configuration in which conductors 10a, 10b, 10c and 10d are not installed, magnetic fluxes pass from left to right as shown in FIG. 9, and a shield effect is unavailable.

According to the separate type magnetic shield apparatus 1 having the configuration of this embodiment, there could be achieved a specific magnetic permeability of 10,000 (this is also the case with the configuration of FIG. 9), a thickness of the magnetic body 22 of 2 mm, a center portion diameter (D) of 60 cm, a width (H1) of 20 cm of the upper and lower joint magnetic shield side walls 4 (4a and 4b) (in this embodiment, a bulkhead magnetic shield member 5 is not provided), an interval of 30 cm between joint magnetic shield side walls 4 (4a and 4b), resulting in a shield ratio of over 1,000.

In addition, since the configuration for performing magnetic shaking permits achievement of a specific magnetic permeability of 500,000, these values are very realistic.

In this embodiment shown in FIG. 8, the outer far magnetic field (H) was 1 G (Gauss); the magnetic field in the gap G of the joint magnetic shield side walls 4 (4a and 4b) was 0.1 G; and that in the cylindrical space S was smaller than 1 mG.

In FIG. 8, magnetic fluxes in the axial line direction of the cylindrical space S (i.e., cylinder axis direction (perpendicular to the paper)), and fluxes in the vertical direction can easily be actively compensated by an opposite phase magnetic field by the application of the technology described in the aforementioned non-patent document 2, i.e., as shown in FIG. 3, by installing a coil 41 on the flange member 6, and installing a coil 42 around the joint magnetic shield side walls 4 and 4. For the purpose of making the first and the second magnetic shield side wall bodies 2A and 2B separable, the coils 41 and 42 are individually separably connected.

The present invention makes it possible to achieve high magnetic shield performance by effectively combining the action of attracting magnetic fluxes of a ferromagnetic body and the action of rebounding magnetic fluxes of current, thus forcedly causing bypassing of magnetic fluxes at discontinuous points even if not a continuous magnetic body.

Therefore, the high-performance separate type magnetic shield apparatus of the present invention can be expected to provide a high accessibility to the shielded space and application in wide areas.

More specifically, the separate type magnetic shield apparatus of the present invention is applicable, for example, to an electron beam exposure device in the industry, for countermeasures for the electron microscope against environmental magnetic field among larger-scale devices, for measurement of brain magnetic field and cardiomagnetic field in the area of measurement, and further, for biomagnetic measurement of animals, and moreover, for measurement in nano-bio area using magnetic beads as a label.

Other Embodiments

In the above-mentioned embodiment 1, the separate type magnetic shield apparatus 1 has been described as having a configuration such that the longitudinal direction of the overall structure becomes horizontal, and as having a magnetic shield side wall body 2 composed of a two-divided body comprising a first magnetic shield side wall body 2A and a second magnetic shield side wall body 2B.

Figure 10A:
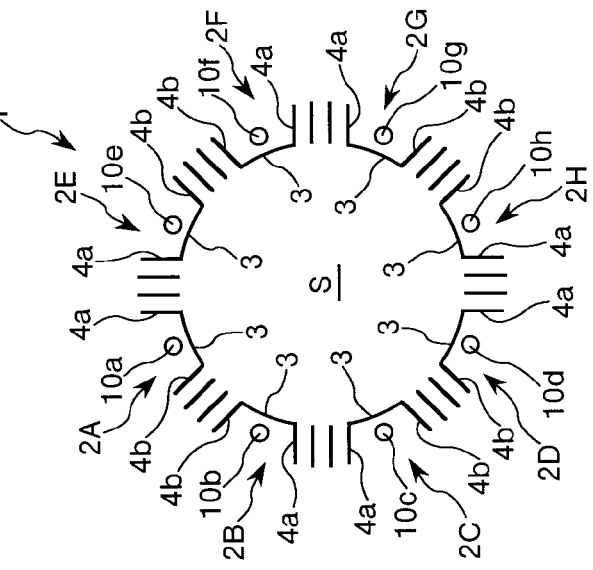
FIGS. 10(*a*), (*b*) and (*c*) are overall configuration views describing other embodiments of the separate type magnetic shield apparatus of the present invention.
Figure 10B:
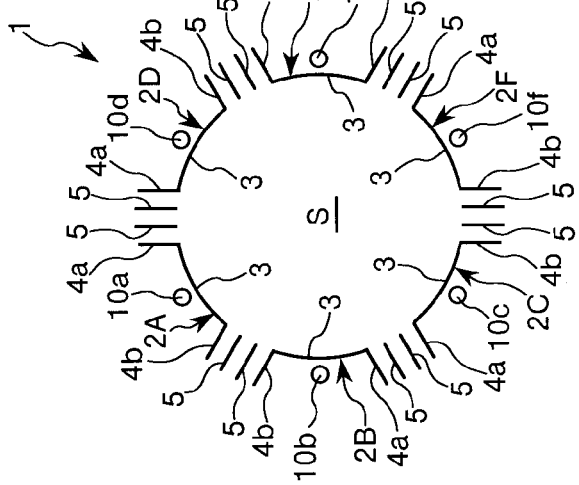
Figure 10C:
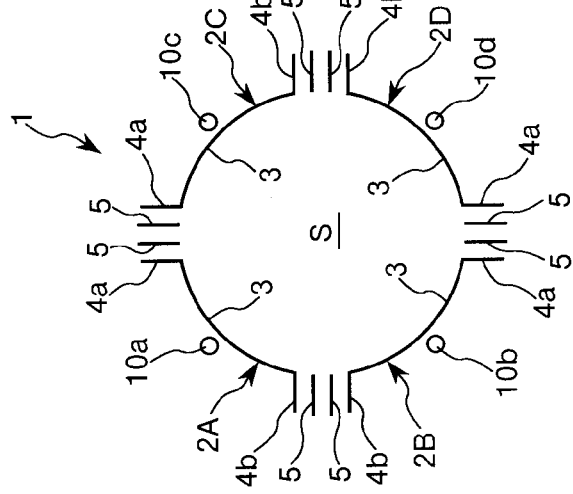

However, the separate type magnetic shield apparatus 1 of the present invention can be composed of four, six or eight, or even more magnetic shield side wall bodies 2, for example as shown in FIGS. 10(*a*), (*b*) and (*c*), when the apparatus becomes larger in size, or when forming an opening on the side is desired.

In other words, the separate type magnetic shield apparatus 1 of the present invention may have a plurality of magnetic shield side wall bodies extending in the longitudinal direction; the plurality of magnetic shield side wall bodies may form, combined with each other, a substantially cylindrical space around the longitudinal axial line extending horizontally in the interior; and at least any one of the magnetic shield side wall bodies may move relative to the remaining magnetic shield side wall bodies, thereby forming a separable configuration.

The separate type magnetic shield apparatus 1 shown in FIG. 10(*a*) has four magnetic shield side wall bodies 2 (2A, 2B, 2C and 2D), and the four magnetic shield side wall bodies 2 form a substantially cylindrical space S around the longitudinal axial line extending horizontally in the interior, combined with each other.

The separate type magnetic shield apparatus shown in FIG. 10(*b*) has six magnetic shield side wall bodies 2 (2A, 2B, 2C, 2D, 2E and 2F), and the six magnetic shield side wall bodies 2, combined with each other, form a substantially cylindrical space S around the longitudinal axial line extending horizontally in the interior.

The separate type magnetic shield apparatus 1 shown in FIG. 10(*c*) has eight magnetic shield wall bodies 2 (2A, 2B, 2C, 2D, 2E, 2F, 2G and 2H), and the eight magnetic shield side wall bodies, combined with each other, form a substantially cylindrical space S around the longitudinal axial line extending horizontally in the interior.

Even in these embodiments, each magnetic shield side wall body 2 has a configuration similar to that of the magnetic shield side wall body 2 described in embodiment 1, and each has a magnetic shield outer side wall 3 having magnetic bodies combined with each other, forming a cylindrical space S in the interior, and joint magnetic shield side walls 4 (4*a* and 4*b*) having magnetic bodies projecting outward in the radial direction from the both-end edges of the magnetic shield outer side wall 3.

Furthermore, in this embodiment as in embodiment 1, conductors 10 (10*a* to 10*d*) extending in the longitudinal axial line direction of the cylindrical space S are provided in the embodiment shown in FIG. 10(*a*) on the magnetic shield outer side wall 3 of the magnetic shield side wall body 2; conductors 10 (10*a* to 10*f*) extending in the longitudinal axial line direction of the cylindrical space S are provided in the embodiment shown in FIG. 10(*b*); and conductors 10 (10*a* to 10*h*) extending in the longitudinal axial line direction of the cylindrical space S are provided in the embodiment shown in FIG. 10(*c*). Current is caused to flow through these conductors in a prescribed direction, and disturbing magnetic fluxes coming horizontally from the magnetic shield side wall bodies on one side to the magnetic shield side wall bodies on the other side are prevented from flowing into the cylindrical space S by deflecting the fluxes up or down by means of magnetic field produced around the conductors.

In an example, in the embodiment shown in FIG. 10(*a*), a current is caused to flow through the conductors 10*a*, 10*c* from the near side in the drawing to the far side, and through the conductors 10*b* and 10*d* from the far side to the near side. In the embodiment shown in FIG. 10(*b*), a current is caused to flow through the conductors 10*a* and 10*d* from the near side to the far side in the drawing, through the conductors 10*c* and 10*f*, from the far side to the near side, and through the conductors 10*b* and 10*e*, a direction of current flow can be appropriately determined, depending upon the direction of the disturbing magnetic field. When the disturbing magnetic field is perfectly horizontal, it is possible even to stop the flow of the current.

In the embodiment shown in FIG. 10(*c*), current is caused to flow through the conductors 10*a*, 10*b*, 10*e* and 10*f* from the near side to the far side in the drawing and through the conductors 10*c*, 10*d*, 10*g* and 10*h*, from the far side to the near side.

The above-mentioned direction of the current is only an example, and the direction may be appropriately changed, depending upon the installation environment of the apparatus.

In the aforementioned embodiments, as in embodiment 1, a plurality of bulkhead magnetic shield members 5 having magnetic bodies are arranged between the opposing both joint shield side walls (4*a*, 4*a*; 4*b*, 4*b*) of the neighboring magnetic shield side wall bodies 2.

Magnetic shield outer side walls 3, joint magnetic shield side walls 4, and bulkhead magnetic shield members 5 are formed by providing magnetic bodies on supports, as in embodiment 1.

In this embodiment also, as in embodiment 1, the structure of each magnetic shield side wall body 2 may have a structure shown in FIG. 6(*a*). A coil may be wound in the longitudinal direction in a toroidal shape on each magnetic shield side wall body 2 as shown in FIG. 6(*b*), and a magnetic shaking current may be caused to flow therethrough.

Although not shown, in this embodiment also, as in embodiment 1, magnetic shield flange members 6 shown in FIG. 5 may be provided at openings in the longitudinal direction of the magnetic shield side wall body 2, and further, current may be caused to flow through a coil installed on this flange member, thereby preventing magnetic fluxes from flowing from the both-end openings in the longitudinal direction of the magnetic shield side wall body into the cylindrical space.

Furthermore, as in embodiment 1, as shown in FIG. 3, current may be caused to flow through a coil wound in the axial line direction around oppositely arranged joint magnetic shield side walls 4 of the neighboring magnetic shield side wall body 2, thereby preventing magnetic fluxes from flowing from the gap formed between joint magnetic shield side walls 4 (4*a*, 4*a*; 4*b*, 4*b*) of the neighboring magnetic shield side wall body 2 into the cylindrical space S.

The magnetic shield side wall bodies 2 surrounding the cylindrical space S have the same dimensions and the same shape, and as described as to embodiment 1, it is possible to provide a space having the lowest density of magnetic flux substantially at the center portion of the cylindrical space S of the separate type magnetic shield apparatus 1, where the magnetic gradient is substantially null.

In the above-mentioned embodiment 1 and other embodiments, the magnetic shield side wall bodies 2, i.e., the magnetic shield outer side walls 3 have been described as having a curved shape. These components may however be linear (i.e., flat-shaped) as the case may be.

The invention claimed is:

1. A separate-type magnetic shield apparatus comprising a plurality of magnetic shield side wall bodies in the longitudinal direction; wherein said plurality of magnetic shield side wall bodies are combined mutually to form therein a substantially cylindrical space around the longitudinal axial line extending horizontally, and at least one of said magnetic shield side wall bodies moves relative to the remaining magnetic shield side wall bodies and is made separable therefrom;
    wherein each of said plurality of magnetic shield side wall bodies has a magnetic shield outer side wall body having one of the magnetic bodies which are combined mutually to form therein said cylindrical space, and joint magnetic shield side walls having magnetic bodies which project from the both longitudinal end edges of said magnetic shield outer wall outwardly in the radial direction to said cylindrical space;
    and wherein conductors extending in the longitudinal axial direction of said cylindrical space are provided on said magnetic shield outer wall of said magnetic shield side wall body to supply current therethrough;
    and whereby disturbing magnetic fluxes coming from said magnetic shield side wall body on one side horizontally to said magnetic shield side wall body on the other side are deflected upwardly or downwardly by means of the magnetic field produced around said conductors to thereby prevent the magnetic fluxes from flowing into said cylindrical space.

2. The separate type magnetic shield apparatus according to claim 1, wherein a plurality of bulkhead magnetic shield members having magnetic bodies are arranged between facing joint magnetic side walls of neighboring magnetic shield side wall bodies.

3. The separate type magnetic shield apparatus according to claim 2, wherein said bulkhead magnetic shield members are formed by providing magnetic bodies on a support.

4. The separate type magnetic shield apparatus according to claim 1, wherein said magnetic shield outer side wall and said joint magnetic shield side wall are formed by providing magnetic bodies on a support.

5. The separate type magnetic shield apparatus according to claim 1, wherein a coil is wound in the longitudinal direction thereof and in a toroidal shape around each of said magnetic shield side wall bodies, and magnetic shaking current is supplied thereto.

6. The separate type magnetic shield apparatus according to claim 1, wherein a magnetic shield flange is provided at each of the both end openings in the longitudinal direction of each magnetic shield side wall body, thereby preventing magnetic fluxes from flowing into said cylindrical space from the longitudinal end openings of said magnetic shield side wall body.

7. The separate type magnetic shield apparatus according to claim 6, wherein said magnetic shield flange member is formed by providing a magnetic body on a support.

8. The separate type magnetic shield apparatus according to claim 6, wherein a coil is installed on said magnetic shield flange member to cause a current to flow threrethrough, thereby preventing magnetic fluxes from flowing into said cylindrical space from the longitudinal openings of said magnetic shield side wall body.

9. The separate type magnetic shield apparatus according to claim 1, wherein a coil is wound around said joint magnetic shield side wall oppositely arranged of said neighboring magnetic shield bodies in the axial direction, and a current is supplied therethrough, thereby preventing magnetic fluxes from flowing from the gap formed between said joint magnetic shield side walls arranged oppositely of the neighboring magnetic shield side wall bodies into said cylindrical space.

10. The separate type magnetic shield apparatus according to claim 1, wherein said cylindrical space is formed by being surrounded by two, four, six or eight said magnetic shield wall bodies.

11. The separate type magnetic shield apparatus according to claim 1, wherein said magnetic shield side wall bodies surrounding said cylindrical space have an identical size and shape.

12. A separate type magnetic shield apparatus comprising a first magnetic shield side wall body and a second magnetic shield side wall body; wherein said first magnetic shield side wall body and said second magnetic shield side wall body form a substantially cylindrical space around the longitudinal axial line extending horizontally in the interior in an oppositely arranged state, and at least any of said magnetic shield side wall bodies moves and is separable from the other magnetic shield side wall body;
    wherein said first and second magnetic shield side wall bodies each has a curved magnetic shield outer side wall which has a magnetic body forming said cylindrical space in the interior in the oppositely arranged state, and joint magnetic shield side walls having magnetic bodies which project vertically from the upper and lower end edges of said curved magnetic shield outer side wall and are spaced apart from each other and facing each other in a oppositely arranged state;
    wherein first and second conductors extending in said longitudinal axial line direction are provided on said curved magnetic shield outer side wall of said first magnetic shield side wall body to cause current to flow;
    wherein first and second conductors extending in said longitudinal axial line are provided on said curved magnetic shield outer side wall of said second magnetic shield side wall body to cause current to flow;
    and whereby disturbing magnetic fluxes coming from said first magnetic shield side wall body horizontally to said second magnetic shield side wall body are deflected up and down by means of magnetic fluxes produced around said first and second conductors, thereby preventing the magnetic fluxes from flowing into said cylindrical space.

13. The separate type magnetic shield apparatus according to claim 12, wherein said first magnetic shield side wall body and the second magnetic shield side wall body have right-left symmetric shapes relative to a vertical plane passing through said longitudinal axial line of said cylindrical space.

14. The separate type magnetic shield apparatus according to claim 12, wherein a plurality of bulkhead magnetic shield members each having a magnetic body are arranged between said joint magnetic shield side walls opposing to each other of said first and second magnetic shield side wall bodies.

15. The separate type magnetic shield apparatus according to claim 14, wherein said bulkhead magnetic shield member is formed by providing a magnetic body in each support.

16. The separate type magnetic shield apparatus according to claim 12, wherein said curved magnetic shield outer side wall and said joint magnetic shield side wall are formed by providing a magnetic body in each of the supports.

17. The separate type magnetic shield apparatus according to claim 12, wherein a coil is wound in a toroidal shape in said axial line direction around said first and second shield side wall bodies, and a magnetic shaking current is supplied thereto.

18. The separate type magnetic shield apparatus according to claim 12, wherein magnetic shield flange members are provided in the axial direction end openings of said first and second shield side wall bodies, thereby preventing magnetic fluxes from flowing from the axial-direction end openings of said first and second shield side wall bodies into said cylindrical space.

19. The separate type magnetic shield apparatus according to claim 18, wherein said magnetic shield flange member is formed by providing a magnetic body in each of the supports.

20. The separate type magnetic shield apparatus according to claim 18, wherein a coil is installed on said magnetic shield flange member to cause current to flow therethrough, thereby preventing magnetic fluxes from the axial-direction end openings of said first and second magnetic shield side wall bodies into said cylindrical space.

21. The separate type magnetic shield apparatus according to claim 12, wherein, around said joint magnetic shield side wall oppositely arranged of said first and second magnetic shield side wall bodies, a coil is wound in the axial line direction to cause current to flow therethrough, thereby preventing magnetic fluxes from flowing from the gap formed between said joint magnetic shield side walls oppositely arranged of said first and second magnetic shield side wall bodies into said cylindrical space.

* * * * *